(12) United States Patent  (10) Patent No.: US 8,196,584 B2
Maguire et al.  (45) Date of Patent: Jun. 12, 2012

(54) ENDOTRACHEAL CUFF AND TECHNIQUE FOR USING THE SAME

(75) Inventors: Seamus Maguire, Athlone (IE); Sean Morris, Athlone (IE); Paul O'Neill, Mullingar (IE); Patrick Joseph Tiernan, Mullingar (IE)

(73) Assignee: Nellcor Puritan Bennett LLC, Boulder, CO (US)

( * ) Notice: Subject to any disclaimer, the term of this patent is extended or adjusted under 35 U.S.C. 154(b) by 1254 days.

(21) Appl. No.: 11/472,915

(22) Filed: Jun. 22, 2006

(65) Prior Publication Data

US 2008/0000482 A1    Jan. 3, 2008

(51) Int. Cl.
*A61M 16/00* (2006.01)
(52) U.S. Cl. .......... 128/207.15; 128/207.14; 128/204.18
(58) Field of Classification Search ............. 128/200.26, 128/204.18, 207.14–207.15; 600/115, 116; 606/108; 604/101.01–102.02, 96.01
See application file for complete search history.

(56) References Cited

U.S. PATENT DOCUMENTS

| | | | |
|---|---|---|---|
| 2,927,584 A | 3/1960 | Wallace |
| 3,769,983 A | 11/1973 | Merav |
| 3,810,474 A | 5/1974 | Cross |
| 3,822,238 A | 7/1974 | Blair et al. |
| 3,913,565 A | 10/1975 | Kawahara |
| 3,971,385 A | 7/1976 | Corbett |
| 3,975,350 A | 8/1976 | Hudgin et al. |
| 3,995,643 A | 12/1976 | Merav |
| 4,022,217 A | 5/1977 | Rowean |
| 4,130,617 A | 12/1978 | Wallace |
| 4,230,108 A | 10/1980 | Young |
| 4,231,365 A | 11/1980 | Scarberry |
| 4,235,239 A | 11/1980 | Elam |
| 4,340,046 A * | 7/1982 | Cox .................. 128/207.17 |
| 4,569,344 A | 2/1986 | Palmer |
| 4,638,539 A | 1/1987 | Palmer |
| 4,649,913 A | 3/1987 | Watson |
| 4,696,296 A | 9/1987 | Palmer |
| 4,700,700 A | 10/1987 | Eliachar |
| 4,791,920 A | 12/1988 | Fauza |
| 4,825,859 A | 5/1989 | Lambert |
| 4,825,861 A | 5/1989 | Koss |
| 4,834,726 A | 5/1989 | Lambert |
| 4,836,199 A | 6/1989 | Palmer |
| 4,838,255 A | 6/1989 | Lambert |
| 4,850,348 A | 7/1989 | Pell et al. |
| 4,856,510 A | 8/1989 | Kowalewski |
| 4,867,153 A | 9/1989 | Lorenzen et al. |

(Continued)

FOREIGN PATENT DOCUMENTS

CA       2353007       6/2000

(Continued)

OTHER PUBLICATIONS

Tecogel brochure page, Noveon Thermedics Polymer Products, Oct. 2003.

(Continued)

*Primary Examiner* — Justine Yu
*Assistant Examiner* — Valerie L Skorupa
(74) *Attorney, Agent, or Firm* — Fletcher Yoder (57) ABSTRACT

An inflatable grooved balloon cuff may be adapted to seal a patient's trachea when associated with an endotracheal tube. Configurations of these cuffs that include grooved regions may provide improved sealing of the trachea by complementing naturally grooved tracheal tissue.

42 Claims, 5 Drawing Sheets

U.S. PATENT DOCUMENTS

| | | | |
|---|---|---|---|
| 4,872,579 A | 10/1989 | Palmer | |
| 4,886,059 A | 12/1989 | Weber | |
| 4,927,412 A | 5/1990 | Menasche | |
| 4,938,741 A | 7/1990 | Lambert | |
| 4,963,313 A | 10/1990 | Noddin et al. | |
| 4,967,743 A | 11/1990 | Lambert | |
| 4,979,505 A | 12/1990 | Cox | |
| 5,019,042 A * | 5/1991 | Sahota | 604/101.01 |
| 5,020,534 A | 6/1991 | Pell et al. | |
| 5,021,045 A | 6/1991 | Buckberg et al. | |
| 5,025,806 A | 6/1991 | Palmer et al. | |
| 5,029,580 A | 7/1991 | Radford et al. | |
| 5,033,466 A | 7/1991 | Weymuller, Jr. | |
| 5,041,125 A * | 8/1991 | Montano, Jr. | 606/192 |
| 5,060,646 A | 10/1991 | Page | |
| 5,065,754 A | 11/1991 | Jensen | |
| 5,074,840 A | 12/1991 | Yoon | |
| 5,076,268 A | 12/1991 | Weber | |
| 5,098,379 A | 3/1992 | Conway et al. | |
| 5,103,816 A | 4/1992 | Kirschbaum et al. | |
| 5,107,829 A | 4/1992 | Lambert | |
| 5,120,322 A | 6/1992 | Davis et al. | |
| 5,122,122 A | 6/1992 | Allgood | |
| 5,133,345 A | 7/1992 | Lambert | |
| 5,135,516 A | 8/1992 | Sahatjian et al. | |
| 5,137,671 A | 8/1992 | Conway et al. | |
| 5,158,569 A | 10/1992 | Strickland et al. | |
| 5,165,420 A | 11/1992 | Strickland | |
| 5,176,638 A | 1/1993 | Don Michael | |
| 5,190,810 A | 3/1993 | Kirschbaum et al. | |
| 5,199,427 A | 4/1993 | Strickland | |
| 5,201,310 A | 4/1993 | Turnbull et al. | |
| 5,207,643 A | 5/1993 | Davis | |
| 5,215,522 A | 6/1993 | Page et al. | |
| 5,218,957 A | 6/1993 | Strickland | |
| 5,230,332 A | 7/1993 | Strickland | |
| 5,233,979 A | 8/1993 | Strickland | |
| 5,246,012 A | 9/1993 | Strickland | |
| 5,250,070 A * | 10/1993 | Parodi | 606/194 |
| 5,251,619 A | 10/1993 | Lee | |
| 5,261,896 A | 11/1993 | Conway et al. | |
| 5,263,478 A | 11/1993 | Davis | |
| 5,269,770 A | 12/1993 | Conway et al. | |
| 5,277,177 A | 1/1994 | Page et al. | |
| 5,285,777 A | 2/1994 | Beckwith | |
| 5,290,585 A | 3/1994 | Elton | |
| 5,304,121 A | 4/1994 | Sahatjian | |
| 5,331,027 A | 7/1994 | Whitbourne | |
| 5,360,402 A | 11/1994 | Conway et al. | |
| 5,370,656 A | 12/1994 | Shevel | |
| 5,370,899 A | 12/1994 | Conway et al. | |
| 5,374,261 A | 12/1994 | Yoon | |
| 5,392,787 A | 2/1995 | Yoon | |
| 5,397,302 A | 3/1995 | Weaver et al. | |
| 5,407,423 A | 4/1995 | Yoon | |
| 5,417,671 A | 5/1995 | Jackson | |
| 5,423,745 A | 6/1995 | Todd et al. | |
| 5,439,457 A | 8/1995 | Yoon | |
| 5,443,063 A | 8/1995 | Greenberg | |
| 5,447,505 A | 9/1995 | Valentine et al. | |
| 5,451,204 A | 9/1995 | Yoon | |
| 5,466,231 A | 11/1995 | Cercone et al. | |
| 5,469,864 A | 11/1995 | Rosenblatt | |
| 5,482,740 A | 1/1996 | Conway et al. | |
| 5,484,426 A | 1/1996 | Yoon | |
| 5,487,730 A | 1/1996 | Maracadis et al. | |
| 5,494,029 A | 2/1996 | Lane et al. | |
| 5,501,669 A | 3/1996 | Conway et al. | |
| 5,507,284 A | 4/1996 | Daneshvar | |
| 5,509,899 A | 4/1996 | Fan et al. | |
| 5,524,642 A | 6/1996 | Rosenblatt | |
| 5,545,132 A | 8/1996 | Fagan et al. | |
| 5,556,391 A | 9/1996 | Cercone et al. | |
| 5,593,718 A | 1/1997 | Conway et al. | |
| 5,599,292 A | 2/1997 | Yoon | |
| 5,599,299 A | 2/1997 | Weaver et al. | |
| 5,599,321 A | 2/1997 | Conway et al. | |
| 5,611,336 A | 3/1997 | Page et al. | |
| 5,613,950 A | 3/1997 | Yoon | |
| 5,649,902 A | 7/1997 | Yoon | |
| 5,653,229 A | 8/1997 | Greenberg | |
| 5,670,111 A | 9/1997 | Conway et al. | |
| 5,674,192 A | 10/1997 | Sahatjian et al. | |
| 5,693,014 A | 12/1997 | Abele et al. | |
| 5,694,922 A | 12/1997 | Palmer | |
| 5,697,365 A | 12/1997 | Pell | |
| 5,700,239 A | 12/1997 | Yoon | |
| 5,715,815 A | 2/1998 | Lorenzen et al. | |
| 5,720,726 A | 2/1998 | Marcadis et al. | |
| 5,722,931 A | 3/1998 | Heaven | |
| 5,730,123 A | 3/1998 | Lorenzen | |
| 5,733,252 A | 3/1998 | Yoon | |
| 5,735,271 A | 4/1998 | Lorenzen et al. | |
| 5,765,559 A | 6/1998 | Kim | |
| 5,769,882 A | 6/1998 | Fogarty et al. | |
| 5,810,786 A | 9/1998 | Jackson et al. | |
| 5,819,733 A | 10/1998 | Bertram | |
| 5,827,215 A | 10/1998 | Yoon | |
| 5,843,017 A | 12/1998 | Yoon | |
| 5,843,028 A | 12/1998 | Weaver et al. | |
| 5,843,060 A | 12/1998 | Cercone | |
| 5,843,089 A | 12/1998 | Sahatjian et al. | |
| 5,868,719 A | 2/1999 | Tsukernik | |
| 5,908,406 A | 6/1999 | Ostapchenko | |
| 5,951,597 A | 9/1999 | Westlund et al. | |
| 5,954,706 A | 9/1999 | Sahatjian | |
| 5,954,740 A | 9/1999 | Ravenscroft et al. | |
| 5,971,954 A | 10/1999 | Conway et al. | |
| 5,976,072 A | 11/1999 | Greenberg | |
| 5,997,503 A | 12/1999 | Willis et al. | |
| 5,997,546 A | 12/1999 | Foster et al. | |
| 6,010,480 A | 1/2000 | Abele et al. | |
| 6,012,451 A | 1/2000 | Palmer | |
| 6,048,332 A | 4/2000 | Duffy et al. | |
| 6,110,192 A | 8/2000 | Ravenscroft et al. | |
| 6,129,547 A | 10/2000 | Cise | |
| 6,152,136 A | 11/2000 | Pagan | |
| 6,169,123 B1 | 1/2001 | Cercone | |
| 6,210,364 B1 | 4/2001 | Anderson et al. | |
| 6,214,895 B1 | 4/2001 | Cercone | |
| 6,227,200 B1 | 5/2001 | Crump et al. | |
| 6,240,321 B1 | 5/2001 | Janke et al. | |
| 6,248,088 B1 | 6/2001 | Yoon | |
| 6,264,631 B1 | 7/2001 | Willis et al. | |
| 6,264,633 B1 | 7/2001 | Knorig | |
| 6,277,089 B1 | 8/2001 | Yoon | |
| 6,312,421 B1 | 11/2001 | Boock | |
| 6,322,586 B1 | 11/2001 | Monroe et al. | |
| 6,364,856 B1 | 4/2002 | Ding et al. | |
| 6,378,521 B1 | 4/2002 | Van Den Berg | |
| 6,394,093 B1 | 5/2002 | Lethi | |
| 6,395,012 B1 | 5/2002 | Yoon et al. | |
| 6,398,266 B1 | 6/2002 | Crump | |
| 6,409,716 B1 | 6/2002 | Sahatjian et al. | |
| 6,481,436 B1 | 11/2002 | Neame | |
| 6,494,203 B1 | 12/2002 | Palmer | |
| 6,524,274 B1 | 2/2003 | Rosenthal et al. | |
| 6,526,977 B1 | 3/2003 | Göbel | |
| 6,543,451 B1 | 4/2003 | Crump et al. | |
| 6,551,272 B2 | 4/2003 | Göbel | |
| 6,572,813 B1 | 6/2003 | Zhang et al. | |
| 6,584,970 B1 | 7/2003 | Crump et al. | |
| 6,588,425 B2 | 7/2003 | Rouns et al. | |
| 6,588,427 B1 | 7/2003 | Carlsen et al. | |
| 6,602,218 B2 | 8/2003 | Yoon | |
| 6,602,219 B2 | 8/2003 | Madsen et al. | |
| 6,609,520 B1 | 8/2003 | Carlsen et al. | |
| 6,612,304 B1 | 9/2003 | Cise et al. | |
| 6,612,305 B2 | 9/2003 | Fauza | |
| 6,613,025 B1 | 9/2003 | Palasis | |
| 6,615,835 B1 | 9/2003 | Cise et al. | |
| 6,620,128 B1 | 9/2003 | Simhambhatla | |
| 6,623,450 B1 | 9/2003 | Dutta | |
| 6,629,530 B2 | 10/2003 | Cise | |
| 6,632,091 B1 | 10/2003 | Cise et al. | |
| 6,651,664 B1 * | 11/2003 | Lomholt | 128/207.14 |
| 6,688,306 B1 | 2/2004 | Cise et al. | |

| | | |
|---|---|---|
| 6,698,424 B2 | 3/2004 | Madsen et al. |
| 6,705,320 B1 | 3/2004 | Anderson |
| 6,722,368 B1 | 4/2004 | Shaikh |
| 6,726,696 B1 | 4/2004 | Houser et al. |
| 6,745,773 B1 | 6/2004 | Gobel |
| 6,767,340 B2 | 7/2004 | Willis et al. |
| 6,769,430 B1 | 8/2004 | Carlsen et al. |
| 6,770,066 B1 | 8/2004 | Weaver et al. |
| 6,786,876 B2 | 9/2004 | Cox |
| 6,790,221 B2 | 9/2004 | Monroe et al. |
| 6,796,309 B2 | 9/2004 | Nash et al. |
| 6,802,317 B2 | 10/2004 | Gobel |
| 6,805,125 B1 | 10/2004 | Crump et al. |
| 6,808,521 B1 | 10/2004 | McMichael |
| 6,814,730 B2 * | 11/2004 | Li .................................. 606/28 |
| 6,890,339 B2 | 5/2005 | Sahatjian et al. |
| 6,908,449 B2 | 6/2005 | Willis et al. |
| 6,916,307 B2 | 7/2005 | Willis et al. |
| 6,923,786 B2 | 8/2005 | Rouns et al. |
| 6,997,909 B2 | 2/2006 | Goldberg |
| 7,040,321 B2 | 5/2006 | Gobel |
| 7,040,322 B2 | 5/2006 | Fortuna |
| 7,066,905 B2 | 6/2006 | Squire et al. |
| 7,147,252 B2 | 12/2006 | Teuscher et al. |
| 7,258,120 B2 | 8/2007 | Carlsen et al. |
| 7,360,540 B2 | 4/2008 | Brain et al. |
| 2001/0016724 A1 * | 8/2001 | Davis et al. .................... 604/509 |
| 2002/0032407 A1 | 3/2002 | Willis et al. |
| 2002/0077603 A1 | 6/2002 | Willis et al. |
| 2002/0077604 A1 | 6/2002 | Willis et al. |
| 2002/0078960 A1 | 6/2002 | Cise |
| 2002/0078963 A1 | 6/2002 | Rouns et al. |
| 2002/0082552 A1 | 6/2002 | Ding et al. |
| 2002/0091375 A1 | 7/2002 | Sahatjian et al. |
| 2002/0193753 A1 | 12/2002 | Rouns et al. |
| 2002/0195110 A1 | 12/2002 | Watton |
| 2003/0000526 A1 | 1/2003 | Gobel |
| 2003/0066532 A1 * | 4/2003 | Gobel ..................... 128/207.15 |
| 2003/0069620 A1 | 4/2003 | Li |
| 2003/0111077 A1 | 6/2003 | Hooser et al. |
| 2003/0116162 A1 | 6/2003 | Madsen et al. |
| 2003/0116963 A1 | 6/2003 | Teuscher et al. |
| 2003/0225369 A1 | 12/2003 | McMichael et al. |
| 2003/0225392 A1 | 12/2003 | McMichael et al. |
| 2003/0225393 A1 | 12/2003 | McMichael et al. |
| 2004/0024363 A1 | 2/2004 | Goldberg |
| 2004/0079376 A1 | 4/2004 | Melker |
| 2004/0092870 A1 | 5/2004 | Squire et al. |
| 2004/0106899 A1 | 6/2004 | McMichael et al. |
| 2004/0106900 A1 | 6/2004 | Triebes et al. |
| 2004/0106901 A1 | 6/2004 | Letson et al. |
| 2004/0116898 A1 | 6/2004 | Hawk |
| 2004/0154623 A1 | 8/2004 | Schaeffer et al. |
| 2004/0193100 A1 | 9/2004 | Van Hooser et al. |
| 2004/0193101 A1 | 9/2004 | Van Hooser et al. |
| 2004/0215142 A1 | 10/2004 | Matheis et al. |
| 2004/0220534 A1 * | 11/2004 | Martens et al. ............... 604/265 |
| 2004/0221853 A1 | 11/2004 | Miller |
| 2004/0255951 A1 | 12/2004 | Grey |
| 2004/0255952 A1 | 12/2004 | Carlsen et al. |
| 2005/0004560 A1 | 1/2005 | Cox |
| 2005/0033267 A1 | 2/2005 | Decaria |
| 2005/0033268 A1 | 2/2005 | Decaria |
| 2005/0033269 A1 | 2/2005 | Decaria |
| 2005/0038381 A1 | 2/2005 | McMichael |
| 2005/0065468 A1 | 3/2005 | Goebel |
| 2005/0124932 A1 | 6/2005 | Foster et al. |
| 2005/0124935 A1 | 6/2005 | McMichael |
| 2005/0137619 A1 | 6/2005 | Schewe et al. |
| 2005/0166924 A1 | 8/2005 | Thomas et al. |

FOREIGN PATENT DOCUMENTS

| | | |
|---|---|---|
| CA | 2353007 A1 | 6/2000 |
| DE | 4334037 A1 | 4/1995 |
| DE | 19500550 | 7/1996 |
| DE | 19855521 | 6/2000 |
| DE | 19855521 A1 | 6/2000 |
| EP | 0884061 | 6/1998 |
| EP | 0884061 A | 12/1998 |
| EP | 1267981 B1 | 4/2000 |
| EP | 1005877 A2 | 6/2000 |
| EP | 1135184 | 6/2000 |
| GB | 1402255 A | 8/1975 |
| GB | 2168256 | 6/1986 |
| WO | WO 95/22367 | 8/1995 |
| WO | WO 00/27461 | 5/2000 |
| WO | WO 00/32262 A1 | 6/2000 |
| WO | WO 00/32263 | 6/2000 |
| WO | WO 01/97890 A | 12/2001 |
| WO | WO 03/045487 A2 | 6/2003 |
| WO | WO 2004/067262 | 8/2004 |
| WO | WO 2004/101046 A1 | 11/2004 |
| WO | WO 2006/023486 | 3/2006 |

OTHER PUBLICATIONS

Dullenkopf, et al., "Fluid leakage past tracheal tube cuffs: evaluation on the new Microcuff endotracheal tube," *Intensive Care Medicine*, (2003) vol. 29, pp. 1849-1853.

Ayşe Gönen Karakeçili et al.; "Comparison of Bacterial and Tissue Cell Initial Adhesion on Hydrophilic/Hydrophobic Biomaterials," J Biomater. Sci. Polymer Edn, vol. 13, No. 2, pp. 185-196 (2002).

Blunt et al.; "Gel Lubrication of the Tracheal Tube Cuff Reduces Pulmonary Aspiration," 2001 American Society of Anesthesiologists, Inc. Lippincott Williams & Wilkins, Inc.; Anesthesiology, V. 95, No. 2, Aug. 2001.

Shintani; "Modification of Medical Device Surface to Attain Anti-Infection," National Institute of Health Sciences; Trends Biomater. Artif. Organs, vol. 18(1), pp. 1-8 (2004).

Sartomer Application Bulletin; "Functional Acrylic Monomers as Modifiers for PVC Plastisol Formulations," pp. 1-6.

* cited by examiner

ENDOTRACHEAL CUFF AND TECHNIQUE FOR USING THE SAME

BACKGROUND OF THE INVENTION

1. Field of the Invention

The present invention relates to medical devices, and more particularly, to endotracheal devices, such as endotracheal tubes and cuffs.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to control the flow of air, food, fluids, or other substances into the patient. For example, medical devices such as tracheal tubes may be used to control the flow of one or more substances into or out of a patient. In many instances it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, tracheal tubes may be used to control the flow of air or other gases through a patient's trachea. Such tracheal tubes may include endotracheal (ET) tubes, tracheotomy tubes, or transtracheal tubes. To seal these types of tracheal tubes, an inflatable cuff may be associated with these tubes. When inflated, the cuff generally expands into the surrounding trachea to seal the tracheal passage.

However, to fit a range of trachea anatomies with a given size of tracheal tube, cuff diameters are usually about one and a half times the diameter of the average trachea. Therefore, when inserted in an average-sized trachea, such a cuff is unable to fully expand and will fold in on itself within the trachea. These folds may serve as leak paths that allow microbe laden secretions to flow past the cuff and enter the lung.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided an inflatable balloon cuff that includes a proximal opening and a distal opening in a wall of the balloon cuff; and a plurality of annular grooves and annular ridges substantially orthogonal to an imaginary axis connecting the proximal opening and the distal opening of the inflated balloon cuff., wherein the grooves are spaced 1 mm-4 mm apart.

There is also provided a method of manufacturing an inflatable balloon cuff that includes providing a balloon cuff wall with a proximal opening and a distal opening; and providing a plurality of annular grooves and annular ridges in the balloon cuff substantially orthogonal to an imaginary axis connecting the proximal opening and the distal opening of the inflated balloon cuff, wherein the grooves are spaced 1 mm-4 mm apart.

There is also provided an inflatable balloon cuff that includes a proximal opening and a distal opening in a wall of the balloon cuff; and an annular groove nonorthogonal to an imaginary axis connecting the proximal opening and the distal opening of the inflated balloon cuff.

There is also provided a method of manufacturing an inflatable balloon cuff comprising: providing a balloon cuff wall with a proximal opening and a distal opening; and providing an annular groove in the balloon cuff nonorthogonal to an imaginary axis connecting the proximal opening and the distal opening of the inflated balloon cuff.

There is also provided an inflatable balloon cuff that includes: a proximal opening and a distal opening in a wall of the balloon cuff; and a plurality of annular grooves and annular ridges substantially orthogonal to an imaginary axis connecting the proximal opening and the distal opening of the inflated balloon cuff, wherein at least a portion of the balloon cuff is less than 60 microns in thickness.

There is also provided an inflatable balloon cuff that includes: a proximal opening and a distal opening in a wall of the balloon cuff; and a plurality of annular grooves and annular ridges substantially orthogonal to an imaginary axis connecting the proximal opening and the distal opening of the inflated balloon cuff, wherein the cuff walls of the grooves are a different thickness than the cuff walls of the ridges.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It is desirable to provide a medical balloon such as an endotracheal cuff or other medical device that may substantially seal the passage in which the cuff is inserted without forming leak paths through which secretions may pass into the lungs. In accordance with some aspects of the present technique, a medical balloon with grooved regions is provided that is adapted to be used with an endotracheal tube or device.

The grooved balloon cuffs provided herein may provide advantages over a typical cuff. A typical inflatable cuff generally assumes a cylindrical or barrel shape when inflated. Thus, a generally cylindrical cuff has a constant diameter along most of its length when fully inflated. This diameter is typically larger than the size of the tracheal passage. Therefore, when a typical cylindrical cuff is inserted into a patient's trachea and inflated, the cuff walls of the cylinder are unable to inflate to their maximum diameter and may fold in on themselves in order to fit in the trachea, which causes wrinkles and leak paths to form.

A grooved cuff shape may provide an improved seal against a patient's passage. The grooved shape of the cuffs as provided herein results in variable inflated cuff diameters along the axis of the patient's passage. By creating a variable diameter cuff profile, the grooves may interrupt the formation of wrinkles or leak paths in the wider ridges that surround the grooves and may thus improve cuff sealing. Further, the grooves may create a shape that complements the naturally grooved contours of a patient's tracheal walls, allowing the cuff to interact with the tracheal walls more closely to prevent leaks. Additionally, the grooved cuffs may include a tapered shape that may improve cuff sealing through a larger variation in inflated cuff diameters along the length of the cuff. The larger variation may increase the likelihood of a substantial match of one of those diameters to the patient's tracheal diameter. Where the cuff diameter is substantially equal to the tracheal diameter, there is a reduced possibility of wrinkles forming in the cuff. Grooved cuff designs also allow for sealing at lower pressures reducing the risk of patient discomfort during ventilation.

Grooved medical cuffs as provided herein may be used in conjunction with any suitable medical device. In certain embodiments, the grooved cuffs as provided herein may be used in conjunction with a catheter, a stent, a feeding tube, an intravenous tube, an endotracheal tube, a tracheostomy tube, a circuit, an airway accessory, a connector, an adapter, a filter, a humidifier, a nebulizer, or a prosthetic, in various embodiments.

Figure 1:
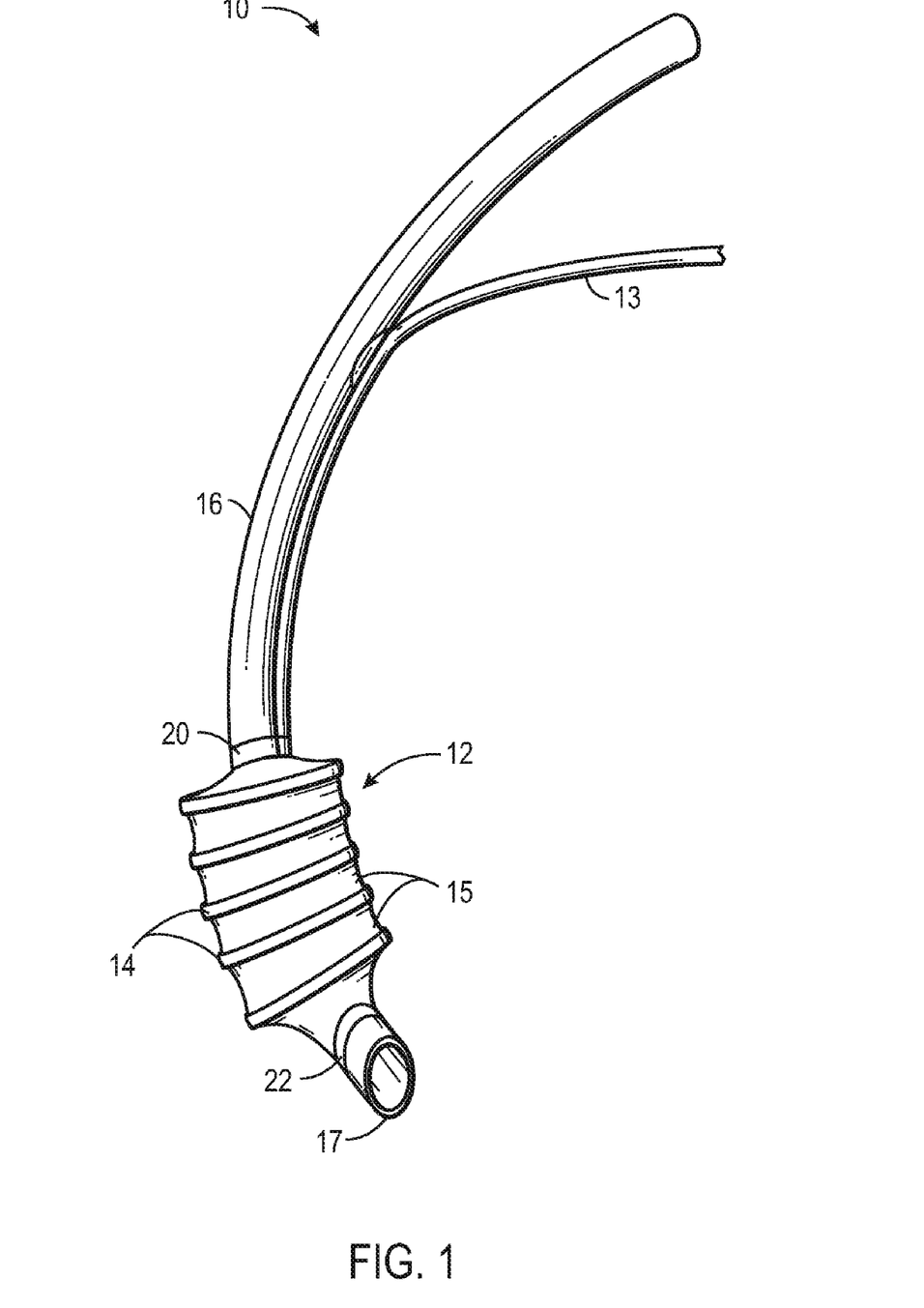
FIG. 1 illustrates an endotracheal tube with an inflatable balloon cuff in accordance with aspects of the present technique.

An example of a grooved inflatable cuff used in conjunction with a medical device is a cuffed endotracheal tube 10, depicted in FIG. 1. The cuffed endotracheal tube 10 includes an inflatable grooved cuff 12 that may be inflated to form a seal against the trachea wall 28 (see FIG. 2). The generally grooved shape includes grooves 15 and ridges 14 that substantially surround the grooves 15. The grooved cuff 12 is disposed on an endotracheal tube 16 that is suitably sized and shaped to be inserted into a patient and allow the passage of air through the endotracheal tube 16. Typically, the cuff 12 is disposed, adhesively or otherwise, towards the distal end 17 of the endotracheal tube 16. The grooved cuff 12 may be inflated and deflated via a lumen 13 in communication with the grooved cuff 12, typically through a hole or notch in the lumen 13. The grooved cuff 12 may generally have an amorphous, or irregular, shape in the uninflated state and may assume the grooved shape when inflated, as depicted. The grooved cuff 12 has a proximal opening 20 and a distal opening 22 formed in the cuff walls 24 to accommodate the endotracheal tube 16.

The grooves 15 and ridges 14 may be characterized by their fully inflated diameters. It should be understood that groove and ridge cuff diameters may be measured when the cuff is fully inflated along an axis that is substantially orthogonal to the axis of the endotracheal tube. A cuff diameter may be measured from cuff wall to cuff wall, either exterior wall to exterior wall or interior wall to interior wall. In certain embodiments, the ridges 14 may have the diameter of an average tracheal diameter or greater. It should be understood that an average trachea size may be an adult male or female average size that is based on height and weight, or a child average size. For example, an adult trachea may range in size from 14 mm to 27 mm, with the average being around 20 mm. The tapered section may include balloon wall diameters between 20 mm and 8 mm when the balloon cuff is fully inflated, which may be appropriate for pediatric size cuffs. In specific embodiments, the grooves 15 may have a diameter that is 95% of the ridge diameter or less In a specific embodiment, it is envisioned that the grooves 15 in general may be closer in size to the tracheal diameter, while the ridges 14 that surround the grooves 15 may be about 1.2× or larger than the tracheal diameter.

The grooves 15 and ridges 14 may also be characterized by the length of each individual groove 15 or ridge 14 along the axis of the tube 16 or the patient's trachea when the cuff is inflated. For example, the grooves 15 and ridges 14 may be at least 1 mm long in one embodiment. In a specific embodiment, the grooves 15 and ridges 14 may be between 1 mm-10 mm along the axis of the tube 16. The grooves 15 and ridges 14 may also be characterized in their total length along the cuff. In certain embodiments, the grooves 15 and ridges 14 are disposed along at least 30% or 10-95% of the total length of the cuff 12 along the axis of the tube 16.

Figure 4A:
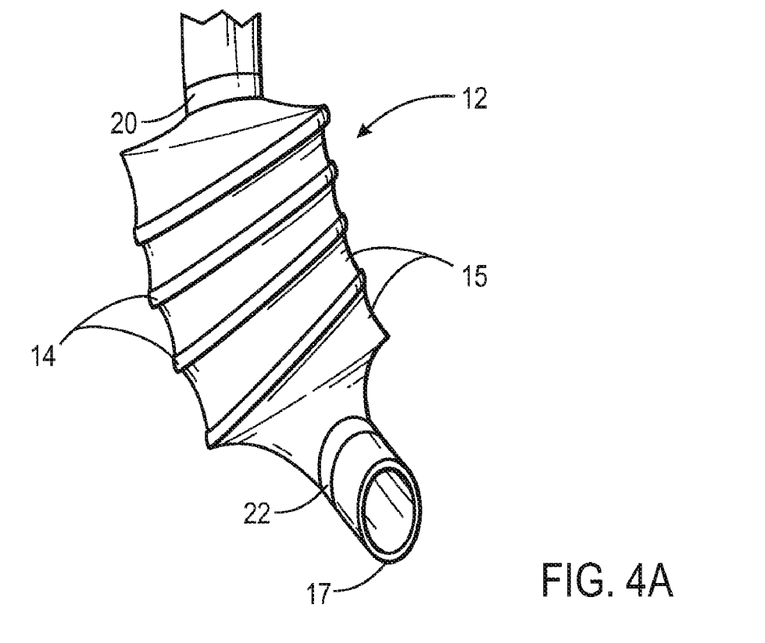
FIG. 4 is an alternative cuff where the pitch of the rings is not constant.

The grooves 15 and ridges 14 may also be characterized by their shape. It is envisioned that the grooves 15 and ridges 14 are substantially annular, which may include partially annular shapes, such as semi-annular or demi-annular shapes. Further, in certain embodiments, the annular grooves 15 and ridges 14 may be disposed slightly off-axis from an axis orthogonal to the tube 16, such as at an angle 5 to 15 degrees off-axis (see FIG. 4A). The grooves 15 and ridges 14 may be characterized by their number. In one embodiment, a grooved cuff 12 may have at least one groove 15 and at least two ridges 14. In other embodiments, a cuff may include more than one groove 15 and more than two ridges 14.

The grooved cuff 12 may be formed from materials having suitable mechanical properties (such as puncture resistance, pin hole resistance, tensile strength), chemical properties (such as forming a suitable bond to the tube 16), and biocompatibility. In one embodiment, the walls of the inflatable cuff 12 are made of a polyurethane having suitable mechanical and chemical properties. An example of a suitable polyurethane is Dow Pellethane® 2363-90A. In another embodiment, the walls of the inflatable cuff 12 are made of a suitable polyvinyl chloride (PVC). Other suitable materials include polypropylene, polyethylene teraphthalate (PETP), low-density polyethylene (LDPE), silicone, neoprene, polyisoprene, or polyurethane (PU)

Figure 2:
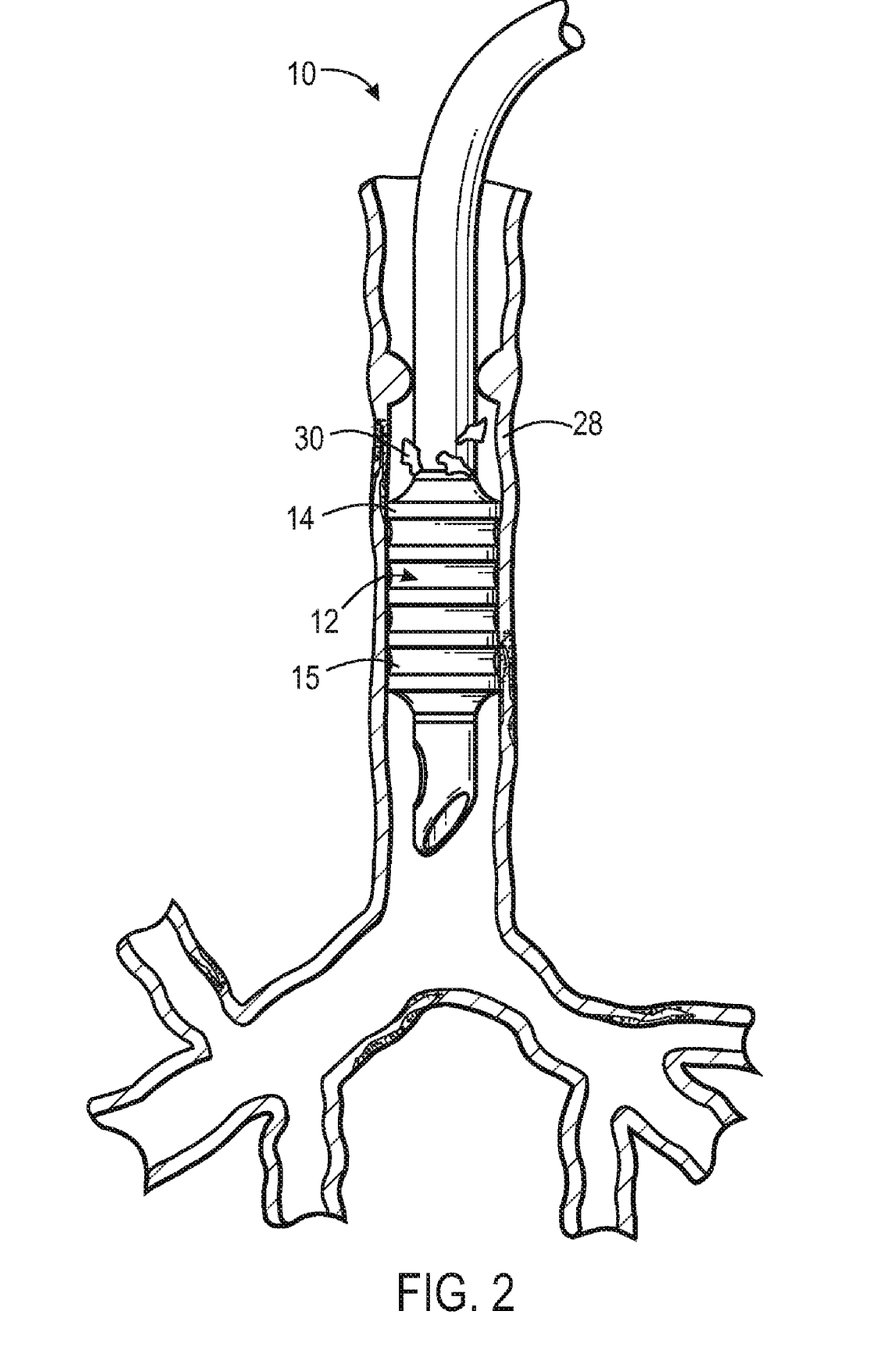
FIG. 2 illustrates the inflatable balloon cuff of the present techniques inserted into a patient's trachea.

FIG. 2 shows the exemplary cuffed endotracheal tube 10 inserted into a patient's trachea. The grooved cuff 12 is inflated to form a seal against the tracheal walls 28 and may prevent secretions 30 or other detritus from passing through the trachea into the lungs. The ridges 14 of the grooved cuff 12 may have fully inflated diameters larger than the diameter of the tracheal passage. As the cuff walls of the ridges 14 inflate within the trachea, they encounter the tracheal walls 28 and are prevented from assuming their fully inflated diameters.

Thus, the grooved cuff 12 in ridged region may be partially flattened against the tracheal walls 28 to create a wrinkled region of the cuff 12. The grooves 15 have cuff wall diameters substantially smaller than the ridged region diameters. The stepwise difference in diameter between the ridges 14 and grooves 15 interrupts the formation of wrinkles. While the ridges 14 may form wrinkles, these wrinkles may be discontinuous from ridge 14 to ridge 14, and thus may be less likely to serve as leak paths for secretions. The grooves 15 may also form wrinkles that are discontinuous. Further, in an embodiment in which the grooves 15 have diameters substantially equal to the tracheal diameter, the grooves may form a wrinkle-free band against the tracheal walls 28, as in this region of the grooved cuff 12, the grooves 15 may assume their fully inflated diameters. In certain embodiments, the grooves may be smaller than the tracheal diameter in order to form wrinkle-free regions that do not contact the tracheal walls 28. In such an embodiment, the grooves 15 may not contribute to the mechanical seal.

Figure 3:
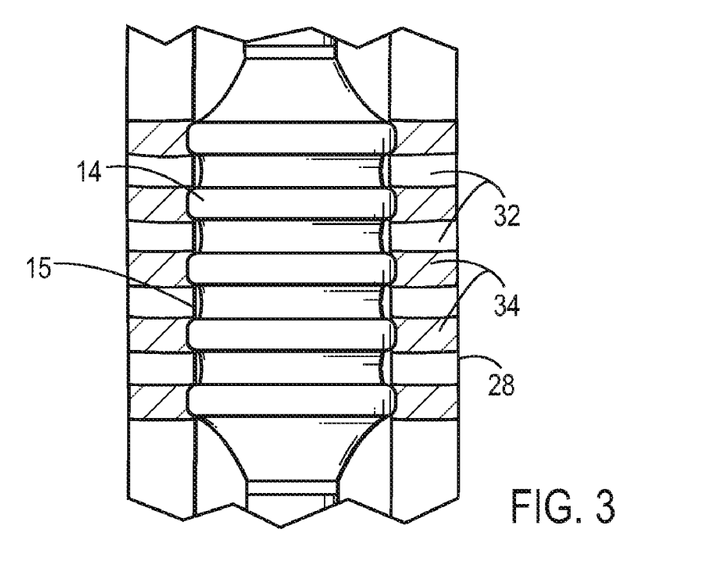
FIG. 3 illustrates the interaction of the endotracheal cuff with cartilage and tissue in the patient's trachea.

As depicted in FIG. 3, the grooved shape of the cuff 12 may result in different regions of the grooved cuff 12 interacting with the tracheal tissue in a variety of manners. The tracheal walls 28 include cartilage rings 32 separated by softer intervening tissue 34 such as fibrous tissue, muscular fibers, mucous membrane, and glands. These cartilage rings 32 may vary from fifteen to twenty in number and may be spaced about 1-4 mm apart along the tracheal walls 28. The grooved shape of the cuff 12 may allow the ridges 14 to align with the relatively softer intervening tissue 34 between the cartilage rings 32. In certain embodiments, the ridges 14 may be designed to be approximately spaced about 1-4 mm apart to facilitate this alignment. This may allow the cuff 12 to conform more closely to the tracheal walls 28, resulting in an improved seal. This may be especially advantageous during ventilation of older patients, as the cartilage rings 32 may harden with patient age.

Figure 4B:
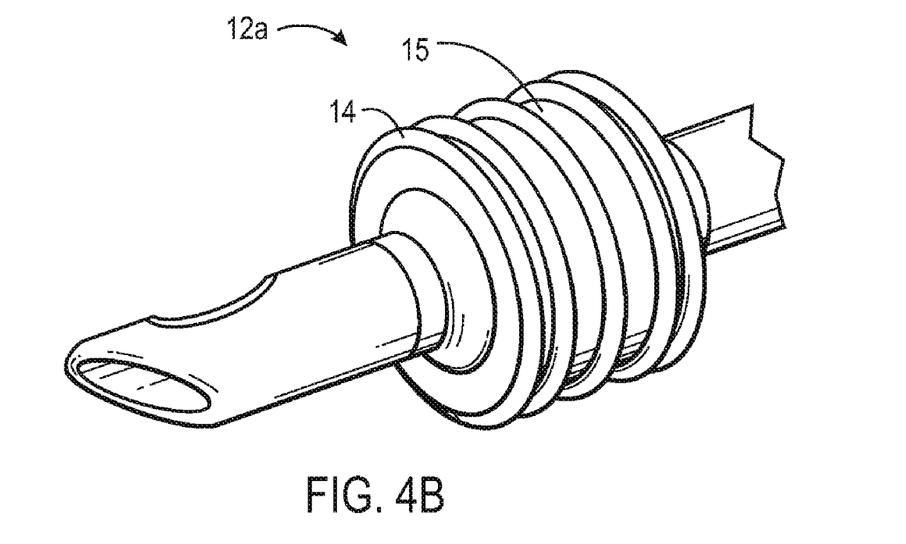

A grooved cuff 12 may have an irregular pitch, as depicted in FIG. 4B. A cuff 12a includes ridges 14 separated by grooves 15 of varying length along the axis of the tube 16. Providing a grooved cuff 12a with an irregular pitch may provide certain advantages. For example, the ridges 14 may be clustered towards the proximal opening 20 of the cuff 12a in order to provide an improved seal against secretions from the mouth. In other embodiments, the ridges 14 may be disposed along the cuff 12a in a manner that may be associated with increased comfort for the patient. For example, the ridges 15 may be clustered together in one region of the cuff and spaced farther apart in other regions in order to minimize cuff contact with the tracheal walls, which may be associated with less discomfort for the patient. Further, it is envisioned that in certain embodiments, the ridges 14 and/or grooves 15 may be of constant or variable length along the axis of the tube 16. In addition, the ridges 14 and grooves 15 may have the same or different length.

Figure 5:
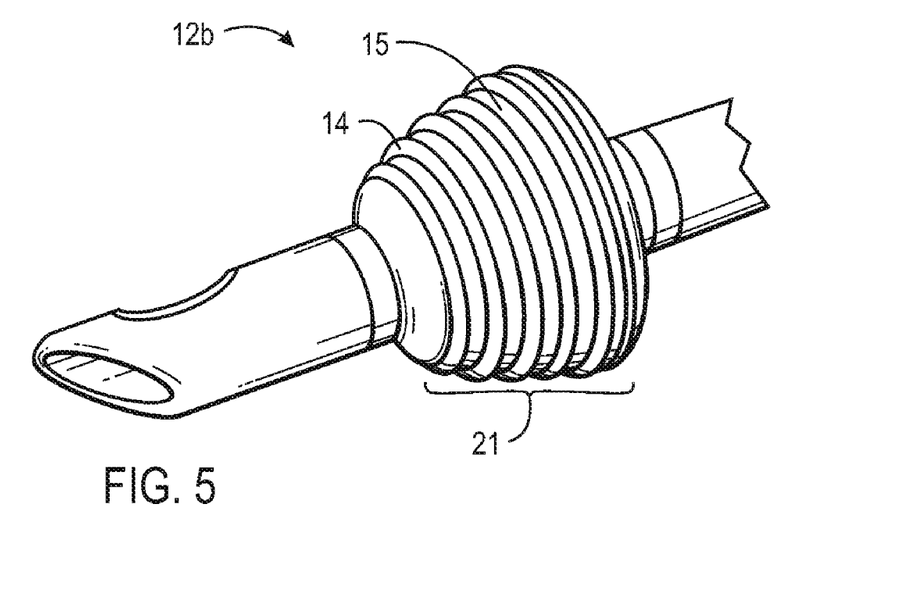
FIG. 5 is an alternative cuff having a taper from the largest diameter ring to a smaller diameter ring.

In certain embodiment, a grooved cuff may assume a tapered configuration, as depicted in FIG. 5. The tapered region of the cuff 12b includes a decrease in the diameters of the ridges 14 and grooves 15 along the length of the taper. One portion of the tapered region of the cuff 12a may include ridges 14, or ridges 14 and grooves 15, with fully inflated diameters larger than the diameter of the tracheal passage. As the cuff walls of this region inflate within the trachea, they encounter the tracheal walls 28 and are prevented from assuming their fully inflated diameters. A portion of the tapered cuff 12 may include ridges 14 and/or grooves 15 with diameters substantially equal to the diameter of the tracheal passage. In such a region, the walls of the cuff 12b may form a wrinkle-free band 34 against the tracheal walls 28, as in this region of the tapered cuff 12, the cuff walls assume their fully inflated diameters. The portion of the tapered region 210f the tapered cuff 12b with ridge 14 and/or groove 15 diameters smaller than the passage may form a minimal contact or no contact region with the tracheal walls 28.

The tapered region 21 may be characterized by the cuff diameters at both ends of the taper. For example, the tapered shape may be described by providing the cuff diameter at the widest point of the taper as well as the cuff diameter at a narrower point. It should be understood that cuff diameters may be measured when the cuff is fully inflated along an axis that is substantially orthogonal to the axis of the endotracheal tube. A cuff diameter may be measured from cuff wall to cuff wall, either exterior wall to exterior wall or interior wall to interior wall. In specific embodiments, the tapered region may narrow from a widest cuff diameter of 30 mm to a narrower diameter of 16.5 mm or smaller. It is envisioned that a cuff may be deigned to accommodate a wide variety of tracheal sizes along a single taper. Thus, a further advantage of a tapered cuff may be its adaptability to patients of a variety of sizes. In one embodiment, certain smaller diameters at the narrow end of the cuff taper are associated with increased sealing performance. For example, certain smaller diameters at the narrow end may maintain the sealing band of the cuff around the trachea even though the tube itself may not be centered in the trachea. Due to the curvature typically built into tracheal tubes for ease of insertion and patient comfort, the tube does not necessarily stay centered in the trachea. By having smaller diameters at the narrow end, it is possible to maintain the benefits of the tapered shape even when the tube is not symmetrically located within the trachea. Thus, in certain embodiments it may be desirable to have cuff diameters less than 16.5 mm or less than 15.24 mm at the narrow end of the cuff.

In other embodiments, the tapered region 21 of the tapered cuff may be characterized by the slope or angle of the taper, which is the included angle of the tapering cuff wall and the axis of an attached endotracheal tube. For example, the angle of the taper may include a tapering angle of at least 15 degrees, at least 20 degrees, or at least 25 degrees. In a specific embodiment, the angle of the taper may be between 17 and 18 degrees. Providing tapering angles greater than 15 degrees generally indicates a greater variance between the widest point and the narrower point of the taper. Further, the tapered region of the tapered cuff may be characterized in certain embodiments by the rate of tapering from the widest point of the taper to a narrower point. A cuff may exhibit a continuous rate of tapering, or a linear tapering, from a wider diameter to a narrower diameter. In other embodiments, the taper may have a nonlinear rate of tapering. For example, it may be advantageous to provide stepwise tapering along the cuff, whereby a certain cuff diameter is maintained for 5-10 mm along the length of the taper. Additionally, a taper may be characterized by its length along the axis of an endotracheal tube. For example, a taper may be along at least 30%, at least 40%, at least 50%, at least 75%, or at least 95% of the length of the cuff along a specific axis.

Figure 6:
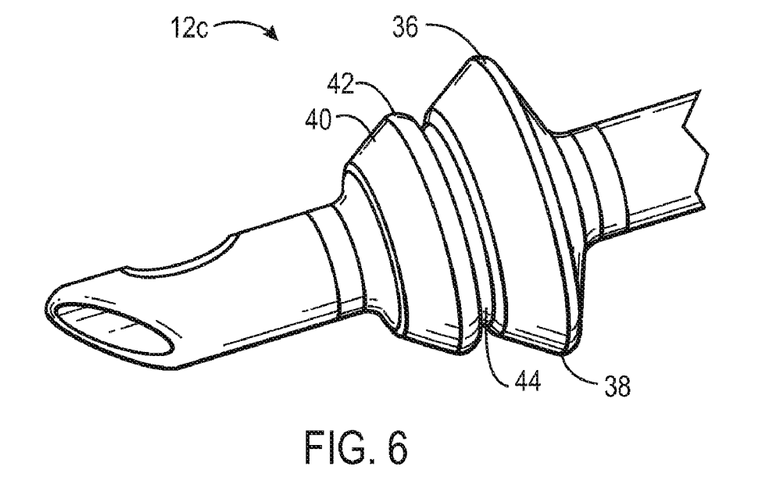
FIG. 6 is an alternative cuff with tapered rings that taper in the same direction.
Figure 7:
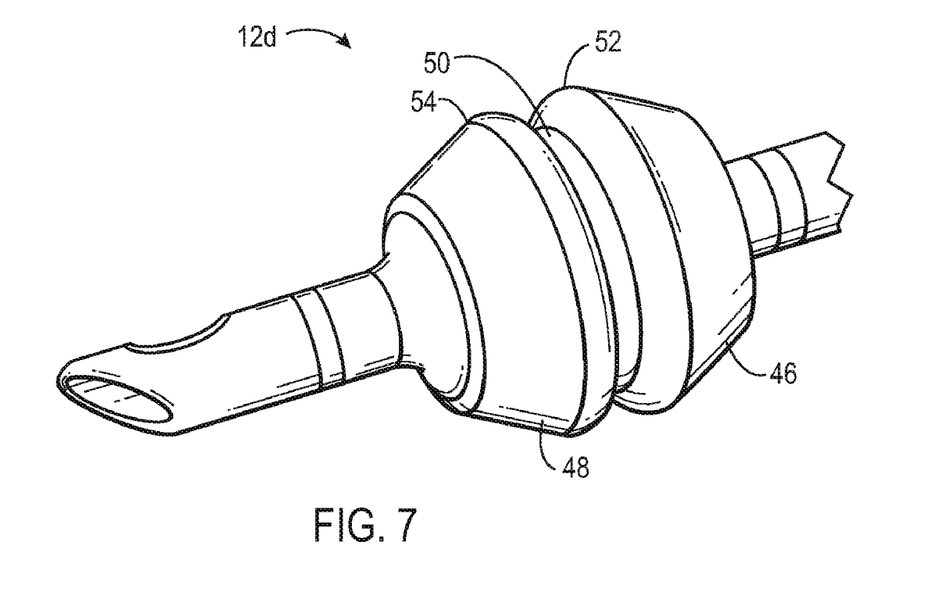
FIG. 7 is an alternative cuff with tapered rings that taper in different directions.

In other embodiments, a cuff 12 may assume a variety of tapered shapes when inflated. For example, referring now to FIGS. 6 and 7, various exemplary cuff shapes are depicted. FIG. 6 depicts an exemplary cuff 12c with two tapered ridges 38 and 42 surrounding a groove 44. The widest diameter 36 of one tapered ridge 38 is substantially larger than the widest diameter 42 of the second tapered ridge 40. In a specific embodiment, the ridge 40 may have a widest diameter 42 that is substantially equal to the narrowest diameter of the first ridge 38. As depicted, both ridges 38 and 42 taper in the same direction. However, it is envisioned that the ridges may also taper in opposite directions. For example, FIG. 7 depicts an exemplary cuff 12d with tapered ridges 46 and 48 that taper in different directions in which the widest diameters 52 and 54 of the tapered ridges 46 and 48 are substantially equal. It is envisioned that cuff 12c and cuff 12d may provide the advantage of providing dual wrinkle-free bands along the tracheal walls when inserted into a patient's trachea. The dual bands may provide improved sealing by providing greater total wrinkle-free contact are with the tracheal walls. In certain embodiments, additional cuff shapes that may form multiple wrinkle-free bands are also contemplated. For example, in one embodiment, multiple tapered ridges may surround a single groove. In other embodiments, the tapered ridge-groove-tapered ridge pattern may be repeated multiple times along the length of the cuff 12. As will be appreciated by those of ordinary skill in the art, may other cuff shapes are within the scope of the present disclosure.

The grooved cuffs as provided herein may be manufactured by a number of techniques, including blow molding, stretch blow molding, extrusion, injection molding, dip molding, casting, or any other suitable technique. The grooved cuffs 12 as provided herein may include cuff walls with constant or varying wall thicknesses along the length of the cuffs. Cuff wall thickness may vary from the widest part of the taper to the narrowest part of the taper. In certain embodiments, it is advantageous to specify cuff wall thickness variation because certain cuff wall thicknesses may be associated with a reduction in wrinkling. In certain embodiments, it may be advantageous to provide a cuff whereby the cuff walls of the grooves are relatively thinner than the cuff walls of the ridges. For example, the cuff walls in the ridges may be at least 1.2×, 1.5×, or 2× thicker than the cuff walls at the narrowest diameter portion of the groove. Such an embodiment may be advantageous because the grooved regions may be more likely to form wrinkle-free bands against the tracheal walls. In certain embodiments, it is contemplated that the cuff walls in the tapered region of the cuff are less than 60 microns in thickness. In another embodiment, the cuff walls are between 10 microns and 3 millimeters in thickness. In specific embodiments, the cuff walls vary along the length of the cuff from between 10 microns to 140 microns in thickness, from between 20 microns to 60 microns in thickness, and from between 30 microns to 50 microns in thickness.

This thickness variation may be accomplished in a number of ways. For example, in one embodiment, the tapered cuffs may be manufactured by an extrusion blow molding process. In this process, a core or mandrel of the extruder has apertures to admit a gas such as pressurized air or an inert gas like nitrogen, into the medical device in the neighborhood of the cuff. After a length of medical device has been extruded, a mold clamps the medical device around the mandrel. As gas is admitted to the cuff area through the mandrel, the cuff expands against the mold. In the alternative, the cuff wall may be expanded in a second discrete expansion process following an extrusion or molding process, such as with a shuttle blow molding process. After initial extrusion, the extruded cuff will have a generally tubular shape with a substantially uniform wall thickness. This tubular shape may then be blown into the tapered shape. This process results in the area of the cuff with larger diameters having thinner walls because the same amount of material is stretched over a larger area. In an alternate embodiment, the wall thickness variation along the length of the taper may be specified in the blow molding process by using a programmable parasin on the extruder. A parasin may also be used to specify a constant wall thickness.

A programmable parasin allows the wall thickness being extruded to be controlled as a function of length. Therefore, the extruded section may have walls of constant or varying thickness. This extruded section may then be blowmolded as described. Other cuff shapes and designs are discussed in the U.S. patent applications titled "ENDOTRACHEAL CUFF AND TECHNIQUE FOR USING THE SAME" to Donald S. Nelson and Dhairya Mehta filed on Jun. 22, 2006, "ENDOTRACHEAL CUFF AND TECHNIQUE FOR USING THE SAME" to Donald S. Nelson and Dhairya Mehta filed on Jun. 22, 2006, and the U.S. patent application titled "THIN CUFF FOR USE WITH MEDICAL TUBING AND APPARATUS FOR MAKING THE SAME" to Joel Colburn and Roger Caluya filed on Jun. 22, 2006, which are hereby incorporated by reference in their entirety.

In certain embodiments, it may be desirable for the grooved cuff 12 to include an antimicrobial surface to prevent the adhesion and propagation of biofilms. The cuff 12 may be formed from hydrophobic polymer with an outer antimicrobial layer that includes a hydrophilic polymer and an antimicrobial compound disposed on an outer surface of the cuff wall. The antimicrobial layer may include an antimicrobial metal, such as copper, silver, or gold. In several exemplary embodiments, the metal may be elemental silver, powdered silver, silver ions ($Ag^+$), or a silver bearing material like silver oxide (AgO). The hydrophilic layer may thus be an antimicrobial (AM) layer. In this way the colonization-inhibiting properties of the hydrophilic surface can be reinforced by anti-microbial properties.

It may be desirable for the metal to be released over time, while the medical device is in use. In one embodiment, therefore, a silver-bearing time-release material may be a phosphorus-based glass material that dissolves in water at a rate that may be a function of its particular formulation. The glass may also contain trace amounts of other elements, such as calcium oxide (CaO). The rate at which silver is released may further be a function of the rate at which the phosphorus-based glass material dissolves in water. The silver, or the phosphorus-based glass material, or both, may be powdered. The release of silver over time, which is defined as the elution rate and is measured in micrograms/$cm^2$/day, may thus be tailored to the specific needs of the application by specifying the formulation of the phosphorus-based glass material. In one embodiment, the silver bearing material may be made up of about 5-10% by weight, e.g. about 7.5% phosphorus-based glass by weight. Such a material is available from Giltech Limited, 12 North Harbour Industrial Estate, Ayr, Scotland, Great Britain KA8 8BN. In one embodiment, the elution rate should be up to about 0.01 micrograms/$cm^2$/day. In another embodiment, the elution rate may be between about 0.01 and 1.0 micrograms/$cm^2$/day. In another embodiment, the elution rate may be about 0.4 micrograms/$cm^2$/day.

In other embodiments, bioactive pharmaceutical agents such as a bronchodilator, an anti-inflammatory agent, or a local anesthetic may be substantially dispersed in a phosphorus-based glass material within a hydrophilic layer. Such bioactive pharmaceutical agents may be delivered to and absorbed by adjacent tissues in substantially the same manner as silver. Regulation and control of dosage, elution rate, and thickness in substantially the same manner as silver may also provide a beneficial pharmacologic or therapeutic action.

A hydrophilic coating may be applied to the surface of a medical device by, e.g., extruding, molding, dipping, spraying, washing, or painting the hydrophilic coating on the surface. In one embodiment, a medical device may be formed by extruding a wall of hydrophobic material along with one or more layers of an antimicrobial material. In another embodiment, a medical device may be formed by molding a wall of hydrophobic material along with one or more layers of an antimicrobial material. The antimicrobial layer may be formed on an inner or an outer surface of the medical device wall. The antimicrobial layer may be comprised of, e.g. polyurethane, such as a medical grade hydrophilic thermoplastic polyurethane into which has been substantially dispersed a silver bearing phosphorus-based glass material. In one embodiment, the antimicrobial layer may be within a range of about 0.002 mm-2.5 mm in thickness, or about 0.13 mm in thickness. In another embodiment, the antimicrobial layer may be within a range of about 0.002 mm-2.5 mm in thickness. In another embodiment, the antimicrobial layer may be up to about 6.35 mm in thickness. In another embodiment, the hydrophobic polymer, hydrophilic polymer and the antimicrobial compound may be compounded together and extruded to form a cuff wall 24.

The tracheal cuffs 12 of the present techniques may be incorporated into systems that facilitate positive pressure ventilation of a patient, such as a ventilator. Such systems may typically include connective tubing, a gas source, a monitor, and/or a controller. The controller may be a digital controller, a computer, an electromechanical programmable controller, or any other control system.

Typically, endotracheal cuffs are inflated within a patient's trachea such that the intra cuff pressure is approximately 20-25 cm $H_2O$. Endotracheal cuffs utilizing inflation pressures significantly greater 25 cm $H_2O$ may be referred to as high-pressure cuffs, while cuffs that are able to effectively seal the trachea at pressures less than 25 cm $H_2O$ may be considered low-pressure cuffs. In certain embodiment, intra cuff inflation pressures of 10-30 cm $H_2O$ may be used with the grooved cuffs of the present techniques.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An inflatable balloon cuff comprising:
   a proximal opening and a distal opening in a wall of the balloon cuff; and
   a plurality of annular grooves and annular ridges substantially orthogonal to an imaginary axis connecting the proximal opening and the distal opening of the inflated balloon cuff, wherein the grooves are spaced between 1 mm-4 mm apart, and wherein the plurality of annular grooves are configured to contact and form a seal against a patient's trachea.

2. The balloon cuff of claim 1, wherein the balloon cuff comprises polyethylene teraphthalate (PETP), low-density polyethylene (LDPE), polyvinyl chloride (PVC), silicone, neoprene, polyisoprene, or polyurethane (PU).

3. The balloon cuff of claim 1, comprising an endotracheal tube coupled to the balloon cuff, wherein the endotracheal tube passes through the proximal and distal openings in the wall of the balloon cuff.

4. The balloon cuff of claim 3, wherein the endotracheal tube is operatively connected to a ventilator.

5. The balloon cuff of claim 1, wherein the plurality of grooves comprise a substantially constant pitch relative to one another.

6. The balloon cuff of claim 1, wherein the balloon cuff comprises at least one tapered region.

7. The balloon cuff of claim 6, wherein the ridges, grooves, or both, taper in diameter to form the tapered region.

8. The balloon cuff of claim 6, wherein the tapered section comprises balloon wall diameters between 40 mm and 8 mm when the balloon cuff is fully inflated.

9. The balloon cuff of claim 6, comprising a second tapered section, wherein the second tapered section tapers in a different direction or the same direction as compared to the first tapered section.

10. The balloon cuff of claim 6, wherein narrowest portion of the tapered section has a balloon diameter that is less than 15 mm when the balloon cuff is fully inflated.

11. The balloon cuff of claim 1, wherein at least one groove or ridge is partially annular.

12. The balloon cuff of claim 1, comprising an antimicrobial coating on at least a portion of the balloon cuff.

13. The balloon cuff of claim 1, wherein at least a portion of the balloon wall is less than 60 microns in thickness.

14. The balloon cuff of claim 1, wherein the balloon wall thickness is between 60 microns and 3 millimeters.

15. The balloon cuff of claim 1, wherein the balloon cuff is asymmetrical along the imaginary axis connecting the proximal opening and the distal opening of the inflated balloon cuff.

16. The balloon cuff of claim 1, wherein the grooves have an irregular pitch relative to one another.

17. A method of manufacturing an inflatable balloon cuff comprising:
    providing a balloon cuff wall with a proximal opening and a distal opening; and
    providing a plurality of annular grooves and annular ridges in the balloon cuff substantially orthogonal to an imaginary axis connecting the proximal opening and the distal opening of the inflated balloon cuff, wherein the grooves are spaced between 1 mm-4 mm apart, and wherein the plurality of annular grooves are configured to contact and form a seal against a patient's trachea.

18. The method of claim 17, wherein the balloon cuff comprises polyethylene teraphthalate (PETP), low-density polyethylene (LDPE), polyvinyl chloride (PVC), silicone, neoprene, polyisoprene, or polyurethane (PU).

19. The method of claim 17, comprising providing an endotracheal tube coupled to the balloon cuff, wherein the endotracheal tube passes through the proximal and distal openings in the wall of the balloon cuff.

20. The method of claim 19 wherein the endotracheal tube is operatively connected to a ventilator.

21. The method of claim 17, wherein the plurality of grooves comprise a substantially constant pitch relative to one another.

22. The method of claim 17, wherein the balloon cuff comprises a tapered region.

23. The method of claim 22, wherein the ridges, grooves, or both taper in diameter to form the tapered region.

24. The method of claim 22, wherein the tapered section comprises balloon wall diameters between 40 mm and 10 mm when the balloon cuff is fully inflated.

25. The method of claim 22, wherein narrowest portion of the tapered section has a balloon wall diameter that is less than 1.52 centimeters when the balloon cuff is fully inflated.

26. The method of claim 17, wherein at least one groove or ridge is partially annular.

27. The method of claim 17, comprising providing an antimicrobial coating on at least a portion of the balloon cuff.

28. The method of claim 17, wherein the balloon wall is less than 60 microns in thickness.

29. The method of claim 17, wherein the balloon wall thickness is between 0.5 millimeters and 3 millimeters.

30. An inflatable balloon cuff for placement in a patient's trachea, wherein the trachea includes a plurality of cartilage rings separated by a plurality of respectively intervening rings of softer tissue, the cuff comprising:
   a proximal opening and a distal opening in a wall of the balloon cuff; and
   a plurality of annular grooves and annular ridges, wherein the plurality of annular grooves and annular ridges are distributed on the inflatable balloon cuff such that when the inflatable balloon cuff is inflated within the patient's trachea, the plurality of grooves are spaced to contact and form a seal against the plurality of cartilage rings in the trachea and the plurality of ridges are spaced to contact and form a seal against the plurality of rings of softer tissue.

31. The balloon cuff of claim 30, wherein the balloon cuff comprises polyethylene teraphthalate (PETP), low-density polyethylene (LDPE), polyvinyl chloride (PVC), silicone, neoprene, polyisoprene, or polyurethane (PU).

32. The balloon cuff of claim 30, comprising at least one ridge nonorthogonal to the imaginary axis connecting the proximal opening and the distal opening of the inflated balloon cuff.

33. The balloon cuff of claim 30, comprising an endotracheal tube coupled to the balloon cuff, wherein the endotracheal tube passes through the proximal and distal openings in the wall of the balloon cuff.

34. The balloon cuff of claim 33, wherein the endotracheal tube is operatively connected to a ventilator.

35. The balloon cuff of claim 30, comprising an antimicrobial coating on at least a portion of the balloon cuff.

36. The balloon cuff of claim 30, wherein the balloon wall varies in thickness along the imaginary axis connecting the proximal opening and the distal opening of the inflated balloon cuff.

37. The balloon cuff of claim 30, wherein the balloon wall is less than 60 microns in thickness.

38. The balloon cuff of claim 30, wherein the balloon wall thickness is between 0.5 millimeters and 3 millimeters.

39. The balloon cuff of claim 30, wherein the balloon cuff comprises five annular ridges and four annular grooves.

40. The balloon cuff of claim 30, wherein the balloon cuff comprises four annular ridges and three annular grooves.

41. The balloon cuff of claim 30, wherein the ridges are configured to only seal against the plurality of rings of softer tissue.

42. A method of manufacturing an inflatable balloon cuff for placement in a patient's trachea, wherein the trachea includes a plurality of cartilage rings separated by a plurality of respectively intervening rings of softer tissue, comprising:
   providing a balloon cuff wall with a proximal opening and a distal opening; and
   providing a plurality of annular grooves and annular ridges in the balloon cuff substantially nonorthogonal to an imaginary axis connecting the proximal opening and the distal opening of the inflated balloon cuff, wherein the plurality of annular grooves and annular ridges are distributed on the inflatable balloon cuff such that when the inflatable balloon cuff is inflated within the patient's trachea, the plurality of grooves are spaced to contact and form a seal against the plurality of cartilage rings in the trachea and the plurality of ridges are spaced to contact and form a seal against the plurality of rings of softer tissue.

* * * * *